US005523499A

United States Patent [19]

Corbin et al.

[11] Patent Number: 5,523,499
[45] Date of Patent: Jun. 4, 1996

[54] PURIFICATION OF HEXAFLUOROETHANE PRODUCTS

[75] Inventors: David R. Corbin, West Chester, Pa.; Richard E. Fernandez, Bear, Del.; Barry A. Mahler, Glen Mills, Pa.

[73] Assignee: E. I. Du Pont de Nemours and Company, Wilmington, Del.

[21] Appl. No.: 295,669

[22] PCT Filed: Mar. 10, 1992

[86] PCT No.: PCT/US92/01607

§ 371 Date: Dec. 28, 1994

§ 102(e) Date: Dec. 28, 1994

[87] PCT Pub. No.: WO93/17988

PCT Pub. Date: Sep. 16, 1993

[51] Int. Cl.⁶ .................................................. C07C 17/38
[52] U.S. Cl. ............................................ 570/179; 570/164
[58] Field of Search ...................................... 570/179, 164

[56] References Cited

U.S. PATENT DOCUMENTS

| 3,026,359 | 3/1962 | Mastrangelo et al. | 260/653 |
|---|---|---|---|
| 4,820,318 | 4/1989 | Chang et al. | 55/68 |
| 4,849,558 | 7/1989 | Goodman | 570/179 |
| 4,902,312 | 2/1990 | Chang | 55/71 |
| 4,906,796 | 3/1990 | Yates | 570/179 |
| 4,940,824 | 7/1980 | Yates | 570/179 |
| 4,940,825 | 7/1990 | Yates | 570/179 |
| 4,950,816 | 8/1990 | Tung et al. | 570/179 |

FOREIGN PATENT DOCUMENTS

| 0389334 | 9/1990 | European Pat. Off. . |
|---|---|---|
| 3311751 | 10/1984 | Germany . |
| 3-72437 | 3/1991 | Japan . |
| WO90/08751 | 8/1990 | WIPO . |

OTHER PUBLICATIONS

Glajch, J. L. et al, "Column Packings for On–Line GC Analysis of Fluorocarbons in the Presence of Reactive Gases", LC–GC, 4(6), 574–577 (1986).

Woytek, A. J., "Appendix 11.11 The role of fluorocarbon gases in the microelectronics industry", *J. Fluor. Chem.*, 33, 331–334 (1986).

Szostak, R., *Molecular Sieves: Principles of Synthesis and Identification*, pp. 2–6, Van Nostrand Reinhold, New York (1989).

*Primary Examiner*—Alan Siegel

[57] ABSTRACT

A process is disclosed for purifying a hexafluoroethane product containing $CClF_3$ and/or $CHF_3$ impurities which comprises the step of contacting the product with a sorbent for said impurities selected from activated carbons and inorganic (i.e. zeolite) molecular sieves. Also disclosed is an improvement to a process for producing $CF_3CF_3$ wherein $CClF_3$ and/or $CHF_3$ impurities are removed from the product utilizing said sorbents.

20 Claims, No Drawings

PURIFICATION OF HEXAFLUOROETHANE PRODUCTS

FIELD OF THE INVENTION

This invention relates to the purification of fluorocarbon products, and more particularly to the purification of hexafluoroethane (i.e., FC-116 or $CF_3CF_3$) products.

BACKGROUND

Products containing hexafluoroethane (i.e., hexafluoroethane products) are produced in various degrees of purity. One type of hexafluoroethane product, resulting for example from the fluorination of a trichlorotrifluoroethane, a dichlorotetrafluoroethane and/or chloropentafluoroethane, often contains significant amounts of chlorotrifluoromethane and/or fluoroform.

Various gaseous fluorine-containing compounds are utilized to etch silica type materials for use in integrated circuits, see e.g., A. J. Woytek, J. Fluor. Chem. 33, 331–334 (1986). A major use of hexafluoroethane is as a plasma etchant in semiconductor device fabrication. It interacts with the surface of the integrated circuit wafer, modifying it so as to lay down the electrical pathways and providing for the surface functionalities that define the integrated circuit. As manufacturers are continually trying to increase the number of functionalities packed per unit surface area, the increasing fineness of surface detail in turn requires greater precision and consistency of the effect the etchant has on the wafer substrate. Products of high purity are critical for this application. It has been found that even very small amounts of impurities can result in wide line width and thus less information bits per chip. Moreover, the presence of trace impurities, including but not limited to particulates, metals, moisture, and other halocarbons in the plasma etchant, even when only present in the part per million level, increase the defect rate in the production of these higher density integrated circuits. As a result there has been continually increasing market demand for higher and higher purity etchants, and an increasing market value of materials having the required purity. Consequently, identification of the offending impurities and their removal represents a significant aspect of preparing the fluorine-containing compounds for these applications.

Purification of halogenated hydrocarbon products has been the subject of considerable research. Of particular interest are the challenges presented in separating a halogenated hydrocarbon from materials such as impurities in the starting materials used to produce the halogenated hydrocarbon, excess reactants, and reaction by-products which are difficult to remove by standard separation methods such as distillation. Selective sorbents have been proposed for various separations. The effectiveness of separation using such sorbents varies according to the chemical components involved; and the successful design of sorbent systems is considered highly dependent upon experimental determination of whether the relative sorbencies of those compounds are suitable for such systems.

SUMMARY OF THE INVENTION

We have found that the chlorotrifluoromethane and/or fluoroform when present as impurities in a hexafluoroethane product can be substantially removed therefrom by using a sorbent for said impurities selected from the group consisting of activated carbons and inorganic molecular sieves (e.g., zeolites). The present invention provides a process for purifying hexafluoroethane product containing impurities including chlorotrifluoromethane and/or fluoroform which comprises the step of contacting said hexafluoroethane product with said sorbent at a temperature within the range of −20° C. to 300° C. and a pressure within the range of 10 kPa to 3000 kPa and for a period of time sufficient to remove a substantial amount of said chlorotrifluoromethane and/or fluoroform. This invention further provides an improvement to a process for producing hexafluoroethane by fluorination of trichlorotrifluoroethane(s), dichlorotetrafluoroethane(s) and/or chloropentafluoroethane to produce a hexafluoroethane product containing chlorotrifluoromethane and/or fluoroform as impurities. This improvement comprises the step of contacting said hexafluoroethane product with said sorbent at a temperature within the range of −20° C. to 300° C. and a pressure within the range of 10 kPa to 3000 kPa and for a period of time sufficient to remove a substantial amount of said chlorotrifluoromethane and/or fluoroform.

The present invention provides a process for producing hexafluoroethane (FC-116) of at least about 99.999% purity.

DETAILS OF THE INVENTION

The present invention provides for the purification of hexafluoroethane products containing the impurities chlorotrifluoromethane and/or fluoroform. A process is provided in accordance with this invention for purifying such hexafluoroethane products which comprises the step of contacting said products with a sorbent for said impurities selected from the group consisting of activated carbons and inorganic molecular sieves at a temperature and a pressure suitable for sorption, for a period of time sufficient to remove a substantial amount of said impurities. The hexafluoroethane product to be purified by this process typically has at least about 90 mole percent hexafluoroethane, preferably has at least 95 mole percent hexafluoroethane, and most preferably has at least about 99 mole percent hexafluoroethane.

Hexafluoroethane products containing chlorotrifluoromethane and/or fluoroform as impurities may result, for example, from a process involving the reaction of anhydrous hydrogen fluoride with 1,1,2-trichloro-1,2,2-trifluoroethane (CFC-113) and 1,2-dichloro-1,1,2,2-tetrafluoroethane (CFC-114) to form chloropentafluoroethane (CFC-115) and hexafluoroethane (FC-116). Unreacted starting materials and CFC-115 may be recycled and reacted further with HF to produce additional FC-116. Additional impurities such as chlorodifluoromethane (HCFC-22), difluoromethane (HFC-32), chloropentafluoroethane and pentafluoroethane (HFC-125) may also be present in such products. Distillation is typically used in order to remove impurities such as hydrogen fluoride and high boilers including tars. Further separation by distillation is typically employed where the amount of impurities is high (e.g., greater than about 10 mole percent), to produce a hexafluoroethane product which has at least about 90 mole percent hexafluoroethane and contains impurities which include chlorotrifluoromethane and/or fluoroform. Further purification of hexafluoroethane using the sorbents of this invention may then be advantageously employed. This invention can thus be adapted to provide an improvement to a process for producing hexafluoroethane by fluorination of materials such as trichlorotrifluoroethanes, dichlorotetrafluoroethanes and/or chloropentafluoroethanes.

Some embodiments of this invention use activated carbon as the sorbent. Commercially available activated carbon may be used. The effectiveness of the process can be influenced by the particular activated carbon employed.

Moreover, the sorption efficiency and sorption capacity of an activated carbon bed depends upon the particle size of the activated carbon in a dynamic flow system. Preferably, the activated carbon has a particle size range of from about 4 to 325 mesh (from about 0.044 to about 4.76 millimeters). More preferably, the activated carbon has a particle size range of from about 6 to 100 mesh (from about 0.149 to about 3.36 millimeters). Most preferably, the activated carbon has a particle size range of from about 10 to 30 mesh (from about 0.595 to about 2.00 millimeters). The sorption capacity of a given activated carbon may also be improved by removing the ash content of the carbon by techniques such as acid wash.

An activated carbon having a particle size range of about 0.595 millimeters×1.68 millimeters (i.e., 12×30 mesh) is available from the Calgon Corporation as Calgon BPL (bituminous coal based) activated granular carbon. Another activated carbon having a particle size range of about 0.074×0.297 millimeters (i.e., 50×200 mesh is available from Barneby & Sutcliffe Corp. as Activated Carbon Type UU (natural grain, coconut shell based) activated carbon.

Some embodiments of this invention use inorganic molecular sieves. Molecular sieves are well known in the art and are defined in R. Szostak, Molecular Sieves-Principles of Synthesis and Identification, Van Nostrand Reinhold (1989) page 2. The inorganic molecular sieves used in this invention include silicas (e.g., zeolites), metalloaluminates and aluminophosphates, as well as other inorganic molecular sieve materials. The molecular sieves useful in the invention will typically have an average pore size of from about 3 to 15 Angstroms.

In some embodiments of this invention zeolite molecular sieve sorbents are used to separate chlorotrifluoromethane and/or fluoroform impurities from FC-116. These materials have silica to alumina mol ratios of about 2:1 to 100:1, or greater. Examples of these materials include H-ZSM-5 zeolites. The zeolites should be dried before use and this is preferably achieved by calcining at from about 100° C. to 300° C. The zeolite may also be pretreated before use with one or more chlorocarbons (e.g., $CCl_4$), chlorofluorocarbons (e.g., $C_2Cl_2F_4$), hydrochlorocarbons (e.g., $CCl_3H$), hydrofluorocarbons (e.g., $CF_3H$) and/or hydrochlorofluorocarbons (e.g., $CF_2ClH$), preferably containing from 1 to 3 carbon atoms.

Suitable temperatures for sorption range from about −20° C. to 300° C. Suitable pressures for sorption range from about 10 kilopascals (kPa) to 3000 kPa.

Contact with the sorbent should be sufficient to achieve the desired degree of FC-116 purity. Preferably, at least about 50 mole percent, total, of the chlorotrifluoromethane and fluoroform present are removed. Preferably, where an activated carbon is used as the sorbent, sufficient contact is provided to remove, in addition to the chlorotrifluoromethane and/or fluoroform, a substantial amount of any chlorodifluoromethane, difluoromethane, chloropentafluoroethane and/or pentafluoroethane present. A particularly advantageous embodiment of this invention involves providing sufficient contact to produce hexafluoroethane of 99.999 mole percent purity.

This invention can be practiced with the sorbent contained in a stationary packed bed though which the process stream containing components for separation is passed. Alternatively, it can be practiced with the sorbent applied as a countercurrent moving bed; or with a fluidized bed where the sorbent itself is moving. The invention also includes embodiments where the sorbent is contained in a stationary packed bed and the process is configured as a simulated moving bed by changing the point of introduction of the process stream requiring separation (e.g., by using appropriate switching valves).

Following use for purification of the FC-116 product, the sorbent is typically regenerated by desorption of sorbed impurities. Desorption of components held by the sorbent may be effected with the sorbent left in place, or the sorbent may be removed and the desorption effected remotely from where the sorption step occurred. Where the sorbent is left in place the desorbed components may exit the sorbent section in a direction either co-current with the hexafluoroethane product feed (in the same direction as the FC-116 product feed stream was fed) or countercurrent to the hexafluoroethane product feed (in the opposite direction of the FC-116 product feed stream). Desorption may be effected with or without the use of a supplemental purge liquid or gas flow. Where a supplemental purge material is used, it may be a component of the feed such as FC-116 itself, or it may be an alternate material, such as nitrogen. Such supplemental purge materials may be fed either co-currently or countercurrently.

In general, desorption can be effected by changing any thermodynamic variable which is effective in removing the sorbed components from the sorbent. For example, sorption and desorption may be effected using a thermal swing cycle (e.g., where after a period of sorption, the sorbent is heated externally through the wall of the vessel containing it and/or a hot liquid or gas purge material comprising a feed component or a alternate material is fed to the sorbent); or using a pressure swing cycle or vacuum swing cycle, (e.g., where after a period of sorption, the pressure is reduced, optionally to various conditions, such that sorbed components are desorbed). Alternatively, the sorbed components can be removed by use of some type of stripping gas or liquid, fed co-current or countercurrent to the original process feed material. The stripping material may be one of the process feed materials or another material such as nitrogen.

One or several beds of sorbent may be used. Where several beds are used, they may be combined in series or in parallel. The separation efficiency may be increased by use of cycling zone sorption, where the pressure and or the temperatures of several beds are alternately raised and lowered as the process stream is passed through.

The production of purified hexafluoroethane may be accompanied by the production of other products which are enriched with regard to the concentration of one or more impurities.

Practice of the invention will be further apparent from the following non-limiting Examples.

EXAMPLES

Example I

Metal tubing (0.18 inch I.D.×12 inches) was packed with either Barneby & Sutcliffe (B&S) carbon (3.85 g, 50×200 mesh) or Calgon carbon (2.59 g, 12×30 mesh) as indicated in Table 1 below, and installed in a gas chromatograph equipped with a flame ionization detector. Helium was fed as a carrier gas at 25.8 sccm. 100 microliter to 500 microliter samples of either $CF_3CF_3$ (FC-116) or of $CClF_3$ (CFC-13) were then injected into the carrier stream at several temperatures. The results of these experiments are shown in Table 1. These data show that FC-116 and CFC-13 have different retention times, and thus may be separated using the carbons of this Example.

TABLE 1

| Temp. | Sample size | Elution Time (Min.) | | | |
|---|---|---|---|---|---|
| | | B & S carbon | | Calgon carbon | |
| °C. | μL | FC-116 | CFC-13 | FC-116 | CFC-13 |
| 100 | 500 | 11.97 | 18.21 | 7.60 | 10.63 |
| 150 | 100 | 3.52 | 5.07 | 2.45 | 3.14 |
| 150 | 250 | 3.35 | 4.91 | 2.29 | 3.02 |
| 150 | 500 | 3.13 | 4.60 | 2.12 | 2.81 |
| 200 | 100 | 1.30 | 1.81 | 0.95 | 1.17 |
| 200 | 250 | 1.24 | 1.74 | 0.88 | 1.11 |
| 200 | 500 | 1.13 | 1.62 | 0.79 | 1.05 |

Example II

A packed tube (26 cm×2.12 cm I.D) containing Calgon BPL carbon (46.1 g, 12×30 mesh) was purged with nitrogen continuously for 24 hours at 250° C. and at 1 atmosphere (100 kPa) pressure. While still being purged with nitrogen, the bed was cooled and was maintained 25° C. FC-116 containing 569 ppm CFC-13 was then fed to the bed at 20.9 grams per hour. The results are shown in Table 2.

TABLE 2

| Time (Min.) | FC-116 in [a] | FC-116 out [b] | CFC-13 out [c] |
|---|---|---|---|
| 0 | 0 | 0 | 0 |
| 44 | 0.111 | 0.000 | 0 |
| 108 | 0.272 | 0.161 | — |
| 127 | 0.320 | 0.209 | 0.45 |
| 132 | 0.333 | 0.222 | 0.55 |
| 137 | 0.345 | 0.234 | 0.64 |
| 142 | 0.358 | 0.247 | 0.72 |
| 146 | 0.368 | 0.257 | 0.78 |
| 151 | 0.381 | 0.270 | 0.83 |
| 156 | 0.393 | 0.282 | 0.87 |
| 161 | 0.406 | 0.295 | 0.89 |
| 166 | 0.418 | 0.307 | 0.91 |
| 170 | 0.428 | 0.317 | 0.92 |
| 175 | 0.441 | 0.330 | 0.94 |

[a] FC-116 in represents the total running sum of the moles of $CF_3CF_3$ fed to the column.
[b] FC-116 out represents the total running sum of the moles of $CF_3CF_3$ exiting the column.
[c] CFC-13 out represents the instantaneous concentration of the $CClF_3$ in the FC-116 exiting the column, expressed as multiples of the 569 ppm feed (e.g., 0.5 would equal a 284 ppm CFC-13 concentration in the FC-116 effluent).

The FC-116 first began exiting the column at about 44 minutes, after about 0.111 moles of FC-116 had been fed. The FC-116 flow breakthrough was sharp, and the outlet flow matched the inlet flow virtually immediately. The initial breakthrough of CFC-13 was detected at about 108 minutes. After this 175 minute run, the packed tube was purged with nitrogen at 250° C., and was ready for further use. This example shows that carbon will selectively hold back CFC-13 allowing FC-116 containing less than 10 ppm of CFC-13 followed by FC-116 containing reduced CFC-13 concentrations to be obtained.

Example III

This is an example of a thermal swing cycle alternating a sorption step with a desorption step. The column and carbon packing were the same as those used in Example II above. During the sorption step FC-116 containing 569 ppm CFC-13 was fed to the Calgon carbon packed column at 25° C. and a FC-116 feed rate of 40 g/hr with a back-pressure setting of 1 atmosphere (100 kPa) in the column. When CFC-13 began to break through at the other end of the column, the flow of feed was stopped, and the ends of the column were sealed. The column was then heated to 150° C., and gas was allowed to escape from the column in the direction countercurrent to the original direction of feed, to keep the pressure at 1 atmosphere (100 kPa). When the temperature reached 150° C., FC-116 containing less than 10 ppm of CFC-13 was fed in the direction countercurrent to the original feed to purge the bed, at 5.2 g/hr, and with a back pressure at 1 atmosphere (100 kPa). The column valves were then closed at both ends, and the column cooled to 23° C. The cooling of the bed to 23° C. caused a partial vacuum. The pressure was then brought back to 1 atmosphere (100 kPa) using the high CFC-13 content FC-116 and the cycle was started again. The sorption and desorption steps were then repeated.

The results of the second sorption step are shown in Table 3.

TABLE 3

| Time (Min.) | Temp °C. | FC-116 in [a] | FC-116 out [b] | CFC-13 out [c] |
|---|---|---|---|---|
| 0 | 23 | 0 | 0 | 0.00 |
| 20 | 23 | 0.096 | 0 | 0.00 |
| 53 | 23 | 0.254 | 0.254 | 0.00 |
| 67 | 23 | 0.321 | 0.225 | 0.41 |

[a] FC-116 in represents the total running sum of the moles of $CF_3CF_3$ fed to the column.
[b] FC-116 out represents the total running sum of the moles of $CF_3CF_3$ exiting the column.
[c] CFC-13 represents the instantaneous concentration of the $CF_3CF_3$ in the FC-116 exiting the column, expressed as multiples of the 569 ppm feed (e.g., 0.5 equals 284 ppm CFC-13 in the FC-116 exiting the column).

Breakthrough of FC-116 occurred at about 20 minutes, after feeding about 0.096 moles of FC-116. The breakthrough was very sharp; the outlet flow reaching the inlet flow rate almost immediately. The initial breakthrough of CFC-13 was detected at about 53 minutes. The concentration increase was linear from that point until the experiment was stopped at 67 minutes.

The results of the desorption step which followed are shown in Table 4.

TABLE 4

| Time (Min.) | Temp °C. | FC-116 in [a] | FC-116 out [b] | CFC-13 out [c] |
|---|---|---|---|---|
| 0 | 34 | 0 | 0 | 1.11 |
| 5 | 54 | 0 | 0.022 | 1.44 |
| 10 | 75 | 0 | 0.041 | 1.87 |
| 14 | 106 | 0 | 0.061 | 2.49 |
| 19 | 132 | 0 | 0.078 | 2.95 |
| 24 | 145 | 0 | 0.084 | 3.18 |
| 29 | 150 | 0 | 0.092 | 3.24 |
| 34 | 150 | 0.00318 | 0.095 | 3.29 |
| 39 | 150 | 0.00636 | 0.098 | 3.20 |
| 43 | 150 | 0.00890 | 0.101 | 3.22 |
| 48 | 150 | 0.01209 | 0.104 | 3.16 |
| 53 | 150 | 0.01527 | 0.107 | 3.11 |
| 58 | 150 | 0.01845 | 0.110 | 2.99 |
| 63 | 150 | 0.02163 | 0.113 | 2.86 |
| 67 | 150 | 0.02418 | 0.115 | 2.67 |
| 72 | 150 | 0.02736 | 0.119 | 2.42 |
| 77 | 150 | 0.03054 | 0.122 | 2.06 |
| 82 | 150 | 0.03372 | 0.125 | 1.61 |
| 87 | 150 | 0.03691 | 0.128 | 1.09 |
| 92 | 150 | 0.04009 | 0.131 | 0.66 |
| 96 | 150 | 0.04263 | 0.134 | 0.47 |

TABLE 4-continued

| Time (Min.) | Temp °C. | FC-116 in [a] | FC-116 out [b] | CFC-13 out [c] |
|---|---|---|---|---|
| 101 | 150 | 0.04582 | 0.137 | 0.23 |
| 106 | 150 | 0.049 | 0.140 | 0.00 |

[a] FC-116 in represents the total running sum of the moles of $CF_3CF_3$ fed to the column.
[b] FC-116 out represents the total running sum of the moles of $CF_3CF_3$ exiting the column.
[c] CFC-13 out represents the instantaneous concentration of the $CClF_3$ in the FC-116 exiting the column, expressed as multiples of the 569 ppm feed (e.g., 0.5 equals 284 ppm CFC-13 in the FC-116 exiting the column).

Initially, no FC-116 was fed, but FC-116 exited the column due to the let down of the pressure as the temperature was raised from 23° C. to 150° C. Beginning at 29 minutes, when the temperature reached 150° C., FC-116 containing less than 10 ppm of CFC-13 was fed at 5.2 g/hr. At 106 minutes, the FC-116 flow was stopped.

This example shows the use of a temperature swing cycle as process concept to produce both CFC-13-free and CFC-13-reduced FC-116.

Example IV

This is an example of a thermal swing cycle alternating a sorption step with a desorption step. The column and carbon packing are the same as those used in Example II above. During the sorption step, FC-116 containing 4 ppm $CHF_3$ (HFC-23), 569 ppm CFC-13, 1 ppm $CHF_2CF_3$ (HFC-125), and 18 ppm $CHClF_2$ (HCFC-22) was fed to the carbon bed at 25° C., 15 atmospheres (1500 kPa), and with a FC-116 flow of at 37.6 g/hr. When the CFC-13 began to break through at the other end of the column, the flow of feed was stopped and the column was heated to 150° C. The gas generated from the heating was vented from the column in the direction countercurrent to the original direction of feed, so as to keep the back pressure at 15 atmospheres (1500 kPa). When the temperature reached 150° C., FC-116 containing 1 ppm HFC-23, no CFC-13, 1 ppm HFC-125, and 16 ppm HCFC-22 was fed in the direction countercurrent to the original feed at 5.2 g/hr and at 15 atmospheres (1500 kPa).

Both sides of the column were then closed, the bed was cooled to 23° C. (causing a partial vacuum). The pressure was then brought back to 1 atmosphere (100 kPa) using the high CFC-13 content FC-116 fed cocurrent, and the sorption cycle was started again. The sorption and desorption steps were then repeated.

The results of the second sorption step are shown in Table 5.

TABLE 5

| Time (Min.) | Temp °C. | FC-116 in [a] | FC-116 out [b] | HFC-23 out [c] | CFC-13 out [d] | HFC-125 out [e] | HCFC-22 out [f] |
|---|---|---|---|---|---|---|---|
| 0 | 25 | 0 | 0 | 0 | 0 | 0 | 0 |
| 26 | 25 | 0.118 | 0 | 0 | 0 | 0 | 0 |
| 159 | 25 | 0.722 | 0.604 | 0 | 0.04 | 0 | 0 |
| 164 | 25 | 0.745 | 0.627 | 0 | 0.17 | 0 | 0 |

[a] FC-116 in represents the total running sum of the moles of $CF_3CF_3$ fed to the column (a separate sum is calculated for each sequence).
[b] FC-116 out represents the total running sum of the moles of $CF_3CF_3$ exiting the column (a separate sum is calculated for each sequence).
[c] HFC-23 out represents the instantaneous concentration of the $CHF_3$ in the FC-116 exiting the column expressed as multiples the 4 ppm originally fed.
[d] CFC-13 out represents the instantaneous concentration of the $CClF_3$ in the FC-116 exiting the column expressed as multiples of the 569 ppm originally fed.
[e] HFC-125 out represents the instantaneous concentration of the $CHF_2CF3$ in the FC-116 exiting the column expressed as multiples of the 1 ppm originally fed.
[f] HCFC-22 out represents the instantaneous concentration of the $CHClF_2$ in the FC-116 exiting the column, expressed as multiples of the 18 ppm originally fed.

Breakthough of FC-116 occurred at about 26 minutes, after about 0.118 moles of FC-116 had been fed. The breakthrough was very sharp; the outlet flow reaching the inlet flow rate almost immediately. The initial breakthrough of the first trace component, CFC-13, was detected at about 159 minutes. At 164 minutes the high trace component content FC-116 flow was stopped.

The results of the desorption step which followed are shown in Table 6.

TABLE 6

| Time (Min.) | Temp °C. | FC-116 in [a] | FC-116 out [b] | HFC-23 out [c] | CFC-13 out [d] | HFC-125 out [e] | HCFC-22 out [f] |
|---|---|---|---|---|---|---|---|
| 0 | 25 | 0 | 0 | 0 | 0 | 0 | 0 |
| 4 | 27 | 0 | .0184 | 0 | 1 | 0 | 0 |
| 9 | 47 | 0 | .0355 | 1.70 | 1.25 | 0 | 6.25 |
| 14 | 62 | 0 | .0597 | 3.39 | 1.59 | 0 | 8.75 |
| 20 | 91 | 0 | .0829 | 6.45 | 2.09 | 7 | 9.72 |
| 25 | 120 | 0 | .103 | 8.85 | 2.58 | 14 | 10.21 |

TABLE 6-continued

| Time (Min.) | Temp °C. | FC-116 in [a] | FC-116 out [b] | HFC-23 out [c] | CFC-13 out [d] | HFC-125 out [e] | HCFC-22 out [f] |
|---|---|---|---|---|---|---|---|
| 31 | 145 | 0 | .111 | 9.17 | 2.81 | 18 | 9.17 |
| 36 | 150 | 0 | .121 | 9.25 | 2.88 | 20 | 1.89 |
| 41 | 150 | .0227 | .144 | 6.48 | 3.54 | 27 | 0 |
| 46 | 150 | .0454 | .167 | 1.62 | 3.54 | 24 | 0 |
| 52 | 150 | .0726 | .194 | 0 | 3.39 | 13 | 0 |
| 57 | 150 | .0953 | .217 | 0 | 3.09 | 5 | 0 |
| 62 | 150 | .118 | .240 | 0 | 2.55 | 1 | 0 |
| 68 | 150 | .145 | .267 | 0 | 1.77 | 1 | 0 |
| 73 | 150 | .168 | .290 | 0 | 0.74 | 1 | 0 |
| 78 | 150 | .191 | .313 | 0 | 0.07 | 1 | 0 |

[a] FC-116 in represents the total running sum of the moles of $CF_3CF_3$ fed to the column (a separate sum is calculated for each sequence).
[b] FC-116 out represents the total running sum of the moles of $CF_3CF_3$ exiting the column (a separate sum is calculated for each sequence).
[c] HFC-23 out represents the instantaneous concentration of the $CHF_3$ in the FC-116 exiting the column expressed as multiples the 4 ppm originally fed.
[d] CFC-13 out represents the instantaneous concentration of the $CClF_3$ in the FC-116 exiting the column expressed as multiples of the 569 ppm originally fed.
[e] HFC-125 out represents the instantaneous concentration of the $CHF_2CF3$ in the FC-116 exiting the column expressed as multiples of the 1 ppm originally fed.
[f] HCFC-22 out represents the instantaneous concentration of the $CHClF_2$ in the FC-116 exiting the column, expressed as multiples of the 18 ppm originally fed.

Initially, no FC-116 was fed, but FC-116 came off the column due to the let down of the pressure as the temperature was raised from 23° C. to 150° C. Beginning at 36 minutes, when the temperature reached 150° C., the lower trace component FC-116 was fed at 5.2 g/hr. At 78 minutes, the FC-116 flow was stopped, the column valved off at both ends, and the column cooled to 23° C.

This example shows the use of temperature swing cycle as a process concept and shows higher adsorption capacity at higher pressure. It also includes data on species other than CFC-13, showing the possibility of use for removing a variety of trace components.

Example V

This is an example of a pressure swing cycle alternating a sorption step with a desorption step. The column and carbon packing are the same as those used in Example II above.

During the sorption step, the column was first fed with FC-116 containing 569 ppm CFC-13, at 25° C. and at a FC-116 feed rate of 37.6 g/hr.

As CFC-13 began to exit the column, the flow of feed was shut off, the gas from the system was then vented countercurrent to the direction of the initial feed until the pressure was reduced to 1 atmosphere (100 kPa). During this venting, approximately 0.1 moles of FC-116 was released which had an average concentration of 1024 ppm CFC-13. FC-116 containing less than 10 ppm CFC-13 was then fed countercurrent to the original feed at 37.6 g/hr at 25° C. and at 1 atmosphere (100 kPa). The system was then pressurized to 15.2 atmospheres (1540 kPa) using the FC-116 containing less than 10 ppm CFC-13, and the sorption cycle was started again. The sorption and desorption steps were then repeated.

The results of the second sorption step are shown in Table 7.

TABLE 7

| Time (Min.) | Press. (atm) | FC-116 in [a] | FC-116 out [b] | CFC-13 out [c] |
|---|---|---|---|---|
| 0 | 15.2 | 0 | 0 | 0 |

TABLE 7-continued

| Time (Min.) | Press. (atm) | FC-116 in [a] | FC-116 out [b] | CFC-13 out [c] |
|---|---|---|---|---|
| 147 | 15.2 | 0.667 | 0.667 | 0 |
| 152 | 15.2 | 0.69 | 0.69 | 0.03 |
| 154 | 15.2 | 0.712 | 0.712 | 0.16 |

[a] FC-116 in representing the total running sum of the moles of $CF_3CF_3$ fed to the column.
[b] FC-116 out represents the total running sum of the moles of $CF_3CF_3$ exiting the column.
[c] CFC-13 out represents the instantaneous concentration of the $CClF_3$ in the FC-116 exiting the column, expressed as multiples of the 569 ppm feed (e.g., 0.5 would equal a 284 ppm CFC-13 concentration in the FC-116 exiting the column).

The results of the desorption step which followed are shown in Table 8.

TABLE 8

| Time (Min.) | FC-116 in [a] | FC-116 out [b] | CFC-13 out [c] |
|---|---|---|---|
| 0 |  | 0 | 0 |
| 2 | .009 | .009 | 1.26 |
| 8 | .036 | .036 | 1.24 |
| 13 | .059 | .059 | 2.22 |
| 19 | .086 | .086 | 2.22 |
| 24 | .109 | .109 | 2.23 |
| 29 | .132 | .132 | 2.21 |
| 35 | .159 | .159 | 2.20 |
| 40 | .182 | .182 | 2.15 |
| 46 | .209 | .209 | 2.05 |
| 51 | .232 | .232 | 1.85 |
| 56 | .254 | .254 | 1.58 |
| 62 | .281 | .281 | 1.18 |
| 67 | .304 | .281 | 0.88 |
| 73 | .331 | .338 | 0.55 |
| 78 | .354 | .354 | 0.31 |
| 83 | .377 | .377 | 0.16 |
| 88 | .400 | .400 | 0.00 |

[a] FC-116 in represents the total running sum of the moles of $CF_3CF_3$ fed to the column.
[b] FC-116 out represents the total running sum of the moles of $CF_3CF_3$ exiting the column.

TABLE 8-continued

| Time (Min.) | FC-116 in [a] | FC-116 out [b] | CFC-13 out [c] |
|---|---|---|---|

[c] CFC-13 out represents the instantaneous concentration of the CClF$_3$ in the FC-116 exiting the column, expressed as multiples of the 569 ppm feed i.e., 0.5 would equal a 284 ppm CFC-13 concentration in the 116 exiting the column.

This example shows the use of a pressure swing cycle as a process concept.

Example VI

Metal tubing (⅛ inch O.D.×10 feet) was packed with a commercially available sample of H-ZSM-5 (Si/Al=15). The packed tubing was heated to 400° C. in a nitrogen atmosphere for about 16 hours. The dried zeolite was installed in a gas chromatograph equipped with a flame ionization detector and using helium as a carrier gas (35 SCCM). Samples of either CF$_3$CF$_3$ (FC-116) or of CClF$_3$ (CFC-13) were then injected into the carrier stream at 200° C. The retention time of FC-116 was 32 min. and the retention time of CFC-13 was 40 min. Further runs were made using HFC-125, CFC-115 and HFC-23. The results of these runs are shown in Table 9. These data show that using the zeolite of this Example FC-116 may be separated from CFC-13, HFC-125, CFC-115 and/or HFC-23 because of their higher retention times.

TABLE 9[a]

| Compound | Retention Time (min) | BP (°C.) |
|---|---|---|
| FC-116 | 32 | −78 |
| CFC-13 | 40 | −81 |
| HFC-125 | 96 | −48 |
| CFC-115 | 101 | −39 |
| HFC-23 | 49 | −82 |

(a) The packed column used for these runs had been previously used for other runs involving halogenated hydrocarbons including C$_2$Cl$_2$F$_4$.

Example VII

Metal tubing (¼ inch O.D.×2 feet) was packed with a commercially available sample of Na—Y (Si/Al=2.5) and installed in a gas chromatograph equipped with a flame ionization detector. Helium was used as a carrier gas. Samples (25 μL) of CF$_3$CF$_3$ (FC-116), CClF$_3$ (CFC-13) or of CHF$_3$ (HFC-23) were then injected into the carrier stream at the temperatures shown in Table 10. The retention times are shown in Table 10. These data show that FC-116 and HFC-23 may be separable by Na—Y because of their different retention times.

TABLE 10

| Compound | Temperature (°C.) | Retention Time (min) |
|---|---|---|
| FC-116 | 200 | 2.40 |
| CFC-13 | 200 | 2.50 |
| HFC-23 | 200 | 10.10 |
| FC-116 | 150 | 4.80 |
| CFC-13 | 150 | 4.80 |
| HFC-23 | 150 | 40.50 |
| FC-116 | 100 | 11.20 |
| CFC-13 | 100 | 11.80 |

TABLE 10-continued

| Compound | Temperature (°C.) | Retention Time (min) |
|---|---|---|
| HFC-23 | 100 | >1000 |

Example VIII

Metal tubing (¼ inch O.D.×2 feet) was packed with a commercially available sample of Zeolite 5A (Si/Al=1.0) and installed in a gas chromatograph equipped with a flame ionization detector. Helium was used as a carrier gas. Samples (25 μL) of CF$_3$CF$_3$ (FC-116), CClF$_3$ (CFC-13) or of CHF$_3$ (HFC-23) were then injected into the carrier stream at the temperatures shown in Table 11. The retention times are shown in Table 11. These data show that using the zeolite of this example FC-116 may be separated from HFC-23 and CFC-13 because of their higher retention times.

TABLE 11

| Compound | Temperature (°C.) | Retention Time (min) |
|---|---|---|
| FC-116 | 200 | 0.4 |
| CFC-13 | 200 | 3.2, 11.80[a] |
| HFC-23 | 200 | 12.0 |

[a] CFC-13 impurity

Particular aspects of the invention are included in the Examples. Other embodiments of the invention will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for purifying a hexafluoroethane product containing impurities selected from the group consisting of chlorotrifluoromethane and fluoroform comprising the step of: contacting said hexafluoroethane product with a sorbent for said impurities selected from the group consisting of activated carbons and inorganic molecular sieves at a temperature within the range of −20° C. to 300° C. and a pressure within the range of 10 kPa to 3000 kPa and for a period of time sufficient to remove a substantial amount of said impurities.

2. The process of claim 1 wherein the hexafluoroethane product contains at least about 90 mole percent hexafluoroethane and wherein contact with said sorbent is sufficient to remove at least about 50 mole percent total of said impurities.

3. The process of claim 2 wherein the sorbent is a zeolite having an average pore size of from about 3 to 15 Angstroms.

4. The process of claim 2 wherein the sorbent is H-ZSM-5 zeolite.

5. The process of claim 4 wherein the zeolite is pretreated with one or more chlorocarbons, chlorofluorocarbons, hydrochlorocarbons, hydrofluorocarbons and/or hydrochlorofluorocarbons containing from 1 to 3 carbon atoms.

6. The process of claim 2 wherein the sorbent is an activated carbon.

7. The process of claim 6 wherein the hexafluoroethane product contains at least 95 mole percent hexafluoroethane.

8. The process of claim 6 wherein the hexafluoroethane product contains at least 99 mole percent hexafluoroethane.

9. The process of claim 6 wherein the hexafluroethane product either consists essentially of hexafluoroethane and chlorotrifluoromethane or consisting essentially of hexafluoroethane and both chlorotrifluoromethane and fluoroform.

10. The process of claim 9 wherein contact with said sorbent is sufficient to provide hexafluoroethane of at least about 99.999 mole percent purity.

11. An improved process for producing hexafluoroethane by fluorination of at least one compound selected from the group consisting of trichlorotrifluoroethanes, dichlorotetrafluoroethanes and chloropentafluoroethane to produce a hexafluoroethane product containing chlorotrifluoromethane, fluoroform or both chlorotrifluoromethane and fluoroform as impurities, the improvement comprising the step of: contacting said hexafluoroethane product with an sorbent for said impurities selected from the group consisting of activated carbons and inorganic molecular sieves at a temperature within the rage of −20° C. to 300° C. and a pressure within the range of 10 kPa to 3000 kPa and for a period of time sufficient to remove a substantial amount of said impurities.

12. The improved process for producing hexafluoroethane of claim 11 wherein the sorbent is an activated carbon, wherein the hexafluoroethane product fed to the adsorbent contains at least about 95 mole percent hexafluoroethane, and wherein contact with said adsorbent is sufficient to provide hexafluoroethane of at least about 99.999 mole percent purity.

13. The process of claim 1 wherein contact with said sorbent is sufficient to provide hexafluoroethane of at least about 99.999 mole percent purity.

14. The process of claim 2 wherein contact with said sorbent is sufficient to provide hexafluoroethane of at least about 99.999 mole percent purity.

15. The process of claim 3 wherein contact with said sorbent is sufficient to provide hexafluoroethane of at least about 99.999 mole percent purity.

16. The process of claim 4 wherein contact with said sorbent is sufficient to provide hexafluoroethane of at least about 99.999 mole percent purity.

17. The process of claim 5 wherein contact with said sorbent is sufficient to provide hexafluoroethane of at least about 99.999 mole percent purity.

18. The process of claim 6 wherein contact with said sorbent is sufficient to provide hexafluoroethane of at least about 99.999 mole percent purity.

19. The process of claim 7 wherein contact with said sorbent is sufficient to provide hexafluoroethane of at least about 99.999 mole percent purity.

20. The process of claim 8 wherein contact with said sorbent is sufficient to provide hexafluoroethane of at least about 99.999 mole percent purity.

* * * * *